United States Patent [19]

Wiley

[11] 4,405,779

[45] Sep. 20, 1983

[54] 6-(CARBO-T-BUTOXY)-3-MERCAPTO-4-ACETAMINO-1,2,4-TRIAZIN-5-ONES

[76] Inventor: Richard H. Wiley, 8 Roosevelt Cir., Palo Alto, Calif. 94306

[21] Appl. No.: 281,699

[22] Filed: Jul. 9, 1981

[51] Int. Cl.$^3$ .......................................... C07D 253/06
[52] U.S. Cl. .................................................... 544/182
[58] Field of Search ........................................ 544/182

[56] References Cited

U.S. PATENT DOCUMENTS 4,358,590  11/1982  Wiley .................................. 544/182

Primary Examiner—John M. Ford

[57] ABSTRACT

6-(Carbo-t-butoxy)-; 6-(carbo-t-butoxymethyl)-; and 6-(carbo-t-butoxyethyl)-3-mercapto-4-acetamino-1,2,4-triazin-5-ones are prepared by conversion of the corresponding carboxylic acids via their acetic anhydride reaction products to their t-butyl esters by reaction with t-butyl alcohol. They are useful as herbicides.

3 Claims, No Drawings

6-(CARBO-T-BUTOXY)-3-MERCAPTO-4-ACETAMINO-1,2,4-TRIAZIN-5-ONES

BACKGROUND:

6-Alkyl- (and aryl-) -3-mercapto-4-amino-1,2,4-triazin-5-ones are known and, with their various derivatives, are an important class of herbicides (U.S. Pat. No. 3,966,715; Chem. Ber. 97, 2173 (1964). The 6-carboxy structures are described in my copending application Ser. No. 6/238,480 filed 2/26/81. It is further noted that tert.-butyl derivatives are of particular activity by virtue of their inhibitory effect on enzyme reactions. An important example is metribuzin (Merck Index No. 6027).

DESCRIPTION OF THE INVENTION:

6-(Carbo-t-butoxy)-; 6-(carbo-t-butoxymethyl); and 6-(2-carbo-t-butoxyethyl)-3-mercapto-4-acetamino-1,2,4-triazin-5-ones, previously unknown, are prepared from the corresponding 6-carboxy-; 6-carboxymethyl-; and 6-(2-carboxyethyl)-3-mercapto-4-amino-1,2,4-triazin-5-ones by reaction of the latter with acetic anhydride to form first the 4-acetamino mixed acetic anhydride followed by reaction with t-butyl alcohol in acetonitrile to give the carbo-t-butoxy acetamino products. The reaction is general and can be applied to other carboxy- and carboxyaryl triazinones.

EXAMPLE 1:

6-(2-Carbo-t-butoxyethyl)-3-mercapto-4-acetamino-1,2,4-triazin-5-one. A solution of 2 g. of 6-(2-carboxyethyl)-3-mercapto-4-amino-1,2,4-triazin-5-one, prepared as described in my copending application Ser. No. 6/238,480 (filed 2/26/81) from α-ketoglutaric acid and thicarbohydrazide, in 40 ml of redistilled (b.p. 136°–138° C.) acetic anhydride is refluxed for 7 hours. The acetic acid and excess acetic anhydride are removed by vacuum evaporation at 65° C., first at 20 mm, then at 0.05 mm. The residue is dissolved in 8 ml of dried t-butyl alcohol and 8 ml of dried acetonitrile at 65° C. and held at 65° C. for one hour. The solution is evaporated first at room temperature, then under vacuum over sodium hydroxide to remove the last traces of volatile by-products. The analytical sample is further dried at 55° C. and 0.05 mm for 4 hours over phosphorus pentoxide. The solid product melts at 95°–100° C. and decomposes at 120° C. It is insoluble in water or alcohol at 25° C.; slightly soluble in warm water; soluble in warm ethanol and in acetone. It can be decolorized with carbon (Norit A). Anal. Calcd. for $C_{12}H_{18}O_4N_4S$: C, 45.86; H, 5.73; N, 17.83; S, 10.19. Found: C, 45.47; H, 5.56; N, 17.27; S, 9.84.

EXAMPLE 2:

6-(Carbo-t-butoxy)-3-mercapto-4-acetamino-1,2,4-triazin-5-one. Example 1 is repeated using 1.0 g of 6-carboxy-3-mercapto-4-amino-1,2,4-triazin-5-one, prepared from ketomalonic acid hydrate and thiocarbohydrazide as previously described in my application Ser. No. 6/238,480 (filed 2/26/81), in 30 ml of acetic anhydride. The reaction mixture is heated at 80° C. to dissolve the acid; then for one hour at 90° C. and then for 3 hours at 110° C. The product, isolated as before, melts at 50°–60° C. and is soluble in acetone and alcohol. It decomposes at about 120° C. Anal. Calcd. for $C_{10}H_{14}O_4N_4S$: S, 11.29. Found: S, 11.29.

EXAMPLE 3:

Example 2 is repeated using 1.1 g of the acid in 30 ml of acetic anhydride heated at 90°–95° C. for 2 hours and then at 120° C. for 2 hours. Anal. Calcd. S, 11.19. Found: S, 11.59.

EXAMPLE 4:

6-(Carbo-t-butoxymethyl)-3-mercapto-4-acetamino-1,2,4-triazin-5-one. Example 1 is repeated using 1 g of 6-carboxymethyl)-3-mercapto-4-amino-1,2,4-triazin-5-one, prepared as described in my application Ser. No. 6/238,480 (2/26/81) from oxaloacetic acid and thiocarbohydrazide, in 30 ml of acetic anhydride and is heated at 125°–135° C. for 5 hours. The product melts at 60°–70° C., is insoluble in water, and is soluble in acetone and in alcohol. Anal. Calcd. for $C_{11}H_{16}O_4N_4S$: S, 10.67. Found S, 10.98.

EXAMPLE 5:

Example 4 is repeated using 1 g of the acid in 30 ml of acetic anhydride heated at 110° C. for 5 hours. Anal. Calcd. for S, 10.67. Found: S, 10.79.

EXAMPLE 6:

Mixed anhydride of acetic acid and 6-(2-carboxyethyl)-3-mercapto-4-acetamino-1,2,4-triazin-5-one. The vacuum dried (55° C., 0.05 mm, 4 hours) product obtained from the reaction of acetic anhydride and 6-(2-carboxyethyl)-3-mercapto-4-amino-1,2,4-triazin-5-one at 145° C. (bath temperature) for 8 hours as described in Example 1 (but not reacted with t-butanol) is separated. Mp. 95°–100° C.; dec. 130° C. Insoluble in water, alcohol, and t-butyl alcohol; soluble in acetone, chloroform, and acetonitrile. Anal. Calcd. for $C_{14}H_{20}O_5N_4S$: N, 20.59; S, 11.76. Found: N, 20.56; S, 11.68.

The products of this invention are useful as herbicides of the triazinone type such as Metribuzin (Merck Index Number 6027). The products show injury to weeds in post-emergence tests (Crafts: Chemistry and Mode of Action of Herbicides). Their hydrophobic character and decreased water solubility make them especially useful. The t-butyl group has a specific anti-enzyme activity. These properties are united in a triazinone structure whose preparation avoids environmental problems associated with the manufacture of Metribuzin.

I claim:
1. 6-(Carbo-t-butoxy)-3-mercapto-4-acetamino-1,2,4-triazin-5-one.
2. 6-(Carbo-t-butoxymethyl)-3-mercapto-4-acetamino-1,2,4-triazin-5-one.
3. 6-(2-Carbo-t-butoxyethyl)-3-mercapto-4-acetamino-1,2,4-triazin-5-one.

* * * * *